US007209566B2

(12) United States Patent
Griniasty

(10) Patent No.: US 7,209,566 B2
(45) Date of Patent: Apr. 24, 2007

(54) METHOD AND APPARATUS FOR DETERMINING A NONLINEAR RESPONSE FUNCTION FOR A LOUDSPEAKER

(75) Inventor: Meir Griniasty, Tel Aviv (IL)

(73) Assignee: Intel Corporation, Santa Clara, CA (US)

( * ) Notice: Subject to any disclaimer, the term of this patent is extended or adjusted under 35 U.S.C. 154(b) by 746 days.

(21) Appl. No.: 09/962,503

(22) Filed: Sep. 25, 2001

(65) Prior Publication Data

US 2003/0059056 A1 Mar. 27, 2003

(51) Int. Cl.
*H04R 29/00* (2006.01)
*H04B 3/00* (2006.01)
*A61F 11/06* (2006.01)
*H04M 9/08* (2006.01)

(52) U.S. Cl. ............................ 381/59; 381/56; 381/58; 381/66; 381/71.1; 379/406.01; 379/406.08

(58) Field of Classification Search .................. 381/59, 381/56, 66, 71.4, 96, 103, 71.1, 58; 379/406.01, 379/406.08
See application file for complete search history.

(56) References Cited

U.S. PATENT DOCUMENTS 5,438,625 A * 8/1995 Klippel ........................ 381/96
5,600,718 A * 2/1997 Dent et al. ............. 379/406.06
5,680,450 A * 10/1997 Dent et al. ............. 379/406.08
5,694,476 A * 12/1997 Klippel ........................ 381/96
5,815,580 A * 9/1998 Craven et al. ................ 381/58
6,044,341 A * 3/2000 Takahashi ................... 704/226
6,058,195 A * 5/2000 Klippel ........................ 381/96
6,760,451 B1 * 7/2004 Craven et al. ................ 381/98
6,766,025 B1 * 7/2004 Levy et al. ................... 381/96
6,996,240 B1 * 2/2006 Sasaki ......................... 381/58
2001/0036284 A1 * 11/2001 Leber ........................ 381/94.2
2003/0142832 A1 * 7/2003 Meerkoetter et al. ......... 381/59

FOREIGN PATENT DOCUMENTS

FR 2413009 7/1979
WO WO-0145459 6/2001

OTHER PUBLICATIONS

Kaizer, A.J. M. Modeling of the Nonlinear Response of an Electrodynamic loudspeaker by a Volterra Series Expansion. Journal of the Audio Engineering Society, 35. Audio Engineering Society, New York (Jun. 1, 1987) pp. 421-433.*
Kaizer, A.J. M. Modeling of the Nonlinear Response of an Electrodynamic loudspeaker by a Volterra Series Expansion. Journal of the Audio Engineering Society, 35. Audio Engineering Society, New York (Jun. 1, 1987) pp. 421-433.*

(Continued)

*Primary Examiner*—Vivian Chin
*Assistant Examiner*—Devona E. Faulk
(74) *Attorney, Agent, or Firm*—Schwegman, Lundberg, Woessner & Kluth, P.A.

(57) ABSTRACT

A nonlinear response function of a loudspeaker is determined by an iterative process during which the nonlinear response function and a linear response associated with an echo and microphone are alternately revised.

24 Claims, 4 Drawing Sheets

OTHER PUBLICATIONS

Klippel, Wolfgang J. Adaptive Nonlinear Control of Loudspeaker Systems. J. Audio Eng. Soc., No. 11, Nov. 1998.*

Kaizer, A.J.M. Modeling of the Nonlinear Response of an Electrodynamic Loudspeaker by a Volterra Series Expansiohn. J. Audio. Eng. Soc., vol. 35, No. 6, Jun. 1987.*

Kaizer, A J. M., "Modeling of the NonLinear Response of an Electrodynamic Loudspeaker By a Volterra Series Expansion", *Journal of the Audio Engineering Society*, 35, Audio Engineering Society, New York, US, (Jun. 1, 1987), p. 421-433.

Klippel, W. J., "Adaptive NonLinear Control of Loudspeaker Systems", *Journal of the Audio Engineering Society*, 46, Audio Engineering Society, New York, US, (1998), p. 939-954.

Stenger, A., et al., "An Acoustic Echo Canceller with Compensation of Nonlinearities", *PROC. IX European Signal Precessing Conference* (*EUSIPCO-98*), pp. 969-972, (Sep. 1998).

"International Preliminary Examination Report for corresponding PCT Application No. PCT/US02/27609", (Oct. 4, 2005), 5 pgs.

"International Search Report for corresponding PCT Application No. PCT/US2/27609", (Jul. 4, 2003), 4 pgs.

"Written Opinion for corresponding PCT Application No. PCT/US02/27609", (Apr. 25, 2005), 5 pgs.

"Substantive / Modified Substantive Examination Adverse Report for Malaysian Application No. PI 200223320", (Jun. 23, 2006), 3 pgs.

* cited by examiner

METHOD AND APPARATUS FOR DETERMINING A NONLINEAR RESPONSE FUNCTION FOR A LOUDSPEAKER

FIELD OF THE INVENTION

The invention relates generally to loudspeakers and, more particularly, to techniques and structures for determining the response function of a loudspeaker.

BACKGROUND OF THE INVENTION

Mobile speaker phones for use within automobiles and other vehicles are subject to echo generation within the vehicle. That is, sounds generated by a loudspeaker of the phone can reverberate within the vehicle and be sensed by a microphone of the phone as an echo. To prevent the return of such echos to the far end user, echo cancellation techniques are often employed. To perform echo cancellation, a response function of the entire channel from the input of the loudspeaker to the output of the microphone is often generated. This channel is typically characterized as a series of three filters; namely, a loudspeaker filter, an echo filter, and a microphone filter. Knowing the input signal of the loudspeaker, the response function can be used to estimate the echos that will be present in the output signal of the microphone. These estimated echos can then be subtracted from the output signal of the microphone to significantly reduce the level of the echos therein.

In the past, the loudspeaker filter, the echo filter, and the microphone filter were all modeled as linear filters. It has since been found that loudspeakers, particularly small, less expensive loudspeakers, are more accurately modeled as nonlinear filters. During speaker phone operation within a vehicle, the echo response of the vehicle chamber will be continuously changing. Thus, it is necessary to adapt the response function used by the echo cancellation functionality on line (i.e., during communication operations). It is difficult, however, to adapt a nonlinear filter response on line. For this reason, the nonlinear response function of the loudspeaker, which does not change much during system operation, can be determined offline and then combined with the adapting linear response function of the echo and microphone on line. Past methods for determining the nonlinear response function of a loudspeaker have been complicated and have required expensive test set ups (e.g., an anechoic chamber set up) to perform. There is therefore a need for relatively simple and inexpensive methods and structures for determining nonlinear loudspeaker response functions.

DETAILED DESCRIPTION

Figure 1:
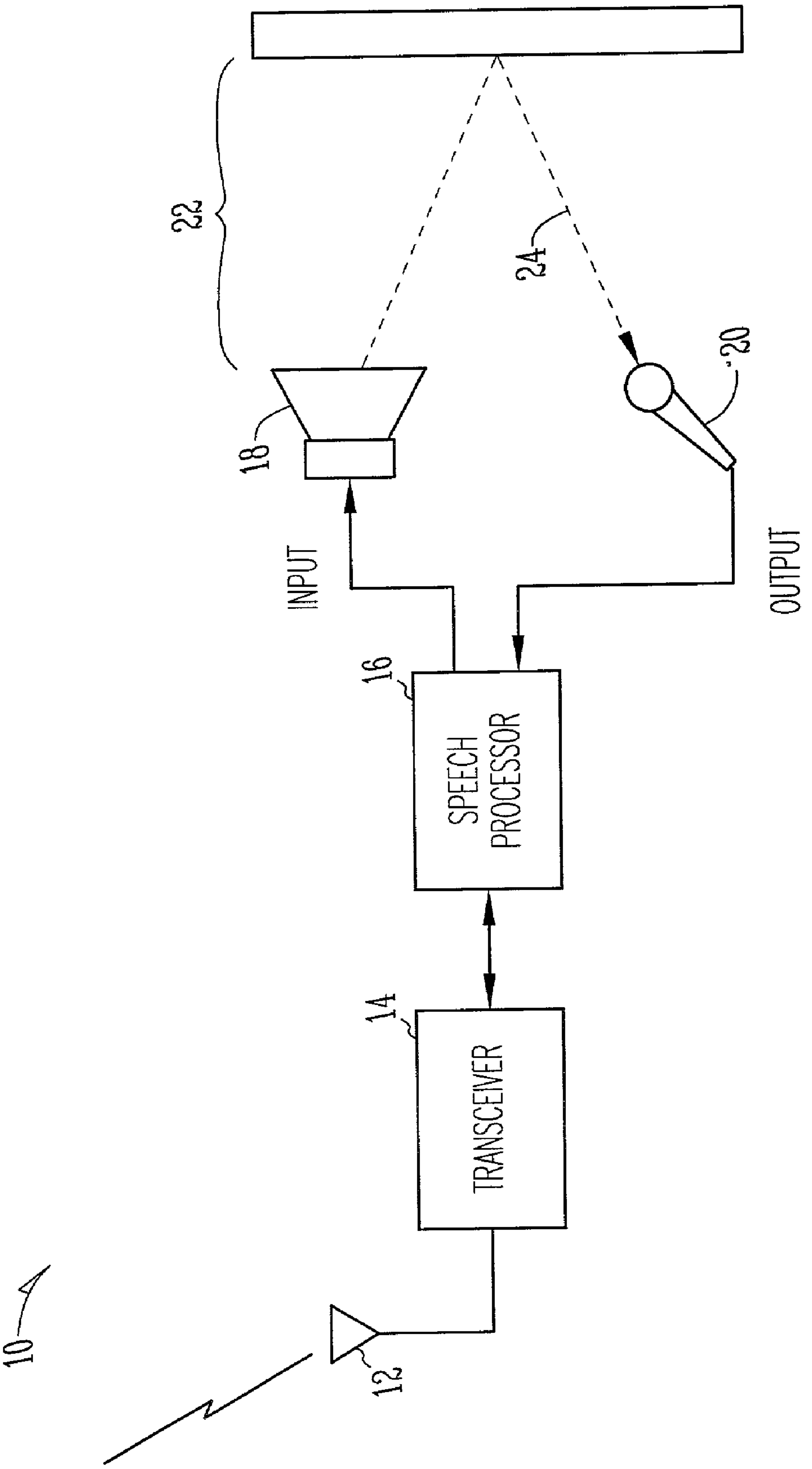
FIG. 1 is a block diagram illustrating a mobile speaker phone system that can be used within a vehicle to provide hands free wireless voice communication between an occupant of the vehicle and a remote party.

In the following detailed description, reference is made to the accompanying drawings that show, by way of illustration, specific embodiments in which the invention may be practiced. These embodiments are described in sufficient detail to enable those skilled in the art to practice the invention. It is to be understood that the various embodiments of the invention, although different, are not necessarily mutually exclusive. For example, a particular feature, structure, or characteristic described herein in connection with one embodiment may be implemented within other embodiments without departing from the spirit and scope of the invention. In addition, it is to be understood that the location or arrangement of individual elements within each disclosed embodiment may be modified without departing from the spirit and scope of the invention. The following detailed description is, therefore, not to be taken in a limiting sense, and the scope of the present invention is defined only by the appended claims, appropriately interpreted, along with the full range of equivalents to which the claims are entitled. In the drawings, like numerals refer to the same or similar functionality throughout the several views.

The present invention relates to methods and structures for determining a nonlinear response function for a loudspeaker in a relatively simple and inexpensive manner. Using the inventive principles, the nonlinear response function of a loudspeaker can be determined without the use of an expensive test setup. In addition, the inventive principles are simple enough to be implemented within an end user device, thus allowing an end user to perform recalibrations of a loudspeaker in the field. In a preferred approach, an iterative process is used during which the response function of the loudspeaker and a combined response function of an echo and microphone are repeatedly and alternately updated and refined. In one technique, cost function minimization processes are used to update the response functions. The iterative process is stopped when a predetermined condition has been satisfied. The inventive principles can be used in connection with any application requiring knowledge of a loudspeaker response function.

FIG. 1 is a block diagram illustrating a mobile speaker phone system 10 that can be used within a vehicle to provide hands free wireless voice communication between an occupant of the vehicle and a remote party. The system 10 can be implemented as, for example, a dedicated standalone unit that is installed within a vehicle. Alternatively, the system 10 can be implemented as a docking station into which a handheld wireless communicator (e.g., a cell phone) is inserted. Other implementations are also possible. As illustrated, the speaker phone system 10 includes: an antenna 12, a wireless transceiver 14, a speech processor 16, a loudspeaker 18, and a microphone 20. The wireless transceiver 14 and associated antenna 12 are operative for supporting communication with a remote transceiver (e.g., within a cellular base station, a communications satellite, etc.) through a wireless communication channel. The speech processor 16 is operative for, among other things, processing speech signals traveling between a local user and the remote party. The loudspeaker 18 and microphone 20 are operative for generating and sensing, respectively, audible signals within an internal chamber 22 of the vehicle.

During outgoing communication, the microphone 20 generates an electrical speech signal at an output thereof based on user speech within the vehicle. The electrical speech signal is delivered to the speech processor 16 which converts the signal into a format required by the wireless transceiver 14. The speech signal delivered to the transceiver 14 can be either digital or analog. The wireless transceiver 14 uses the speech signal received from the speech processor 16 to generate an RF transmit signal that is then transmitted into the wireless channel via antenna 12. During incoming communication, the antenna 12 receives an RF signal from the wireless communication channel and delivers it to the wireless transceiver 14. The wireless transceiver 14 then recovers speech information from the RF signal and delivers the speech information to the speech processor 16. The speech processor 16 uses the speech information to generate an analog speech signal for delivery to the loudspeaker 18. The loudspeaker 18 then generates an audible speech signal within the chamber 22 of the vehicle based on the analog speech signal received from the speech processor 16.

The audible signal generated by the loudspeaker 18 will often reverberate within the internal chamber 22 of the vehicle. As illustrated in FIG. 1, a portion of the audible signal may be directed back toward and sensed by the microphone 20 as an echo signal 24. If ignored, the echo signal will be transmitted back to the remote party as part of the outgoing wireless signal. To prevent this from occurring, echo cancellation techniques are commonly employed. In one echo cancellation technique, a response function is generated that characterizes the response from the input of the loudspeaker 18 to the output of the microphone 20. Once this response function has been generated, it is used to calculate an estimated echo component at the output of the microphone 20 based on the known input signal of the loudspeaker 18. The estimated echo component is then subtracted from the actual output signal of the microphone 20 to reduce the echo level within the signal.

Figure 2:
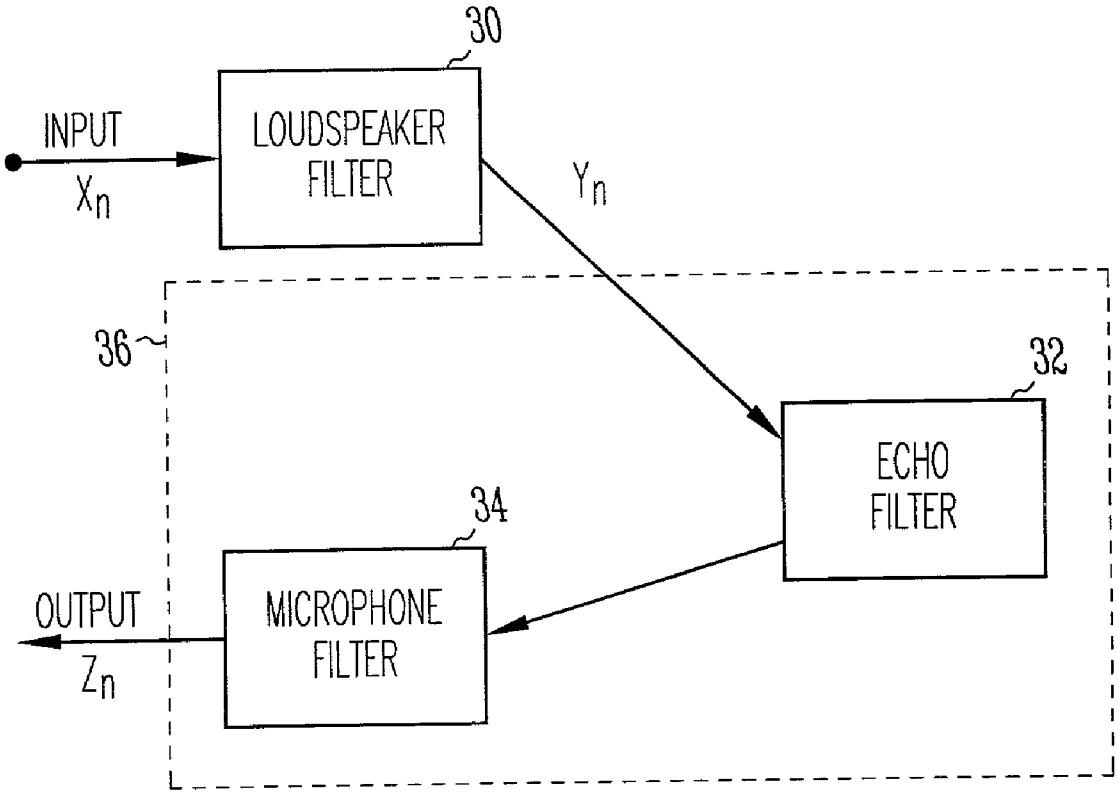
FIG. 2 is a block diagram illustrating a technique for modeling a channel between the input of the loudspeaker and the output of microphone of FIG. 1 for purposes of generating a corresponding response function.

FIG. 2 is a block diagram illustrating one method of modeling the channel between the input of loudspeaker 18 and the output of microphone 20 of FIG. 1 for purposes of generating the response function necessary to perform echo cancellation. As illustrated, the channel is represented as a concatenation of three filters; namely, a loudspeaker filter 30, an echo filter 32, and a microphone filter 34. In the past, each of these filter components was typically characterized as a linear filter and, therefore, a single linear transfer function could be developed for the entire channel. More recently, however, it has been shown that the response function of loudspeakers, particularly small, less expensive loudspeakers, is nonlinear in nature. Such devices are more appropriately modeled as, for example, nonlinear Volterra filters. Because conditions inside a vehicle are usually changing with time (e.g., passengers are entering, exiting, and/or moving about, windows are being opened and closed, etc.), the individual response of the echo filter 32 will also change with time. Therefore, the response function used for echo cancellation will have to adapt during system operation. It is typically very difficult to adapt a nonlinear response function while a system in on-line (i.e., during communication with the remote party). Thus, in one approach, only the combined linear response function 36 of the echo filter 32 and the microphone filter 34 is adapted while the system 10 is on-line. The nonlinear response function of the loudspeaker filter 30, which does not typically change with time, is determined off-line and stored. The nonlinear response function of the loudspeaker 18 is then combined with the adapting linear response function 36 of the echo/microphone (e.g., using convolution) to generate the response function required for echo cancellation.

Figure 3:
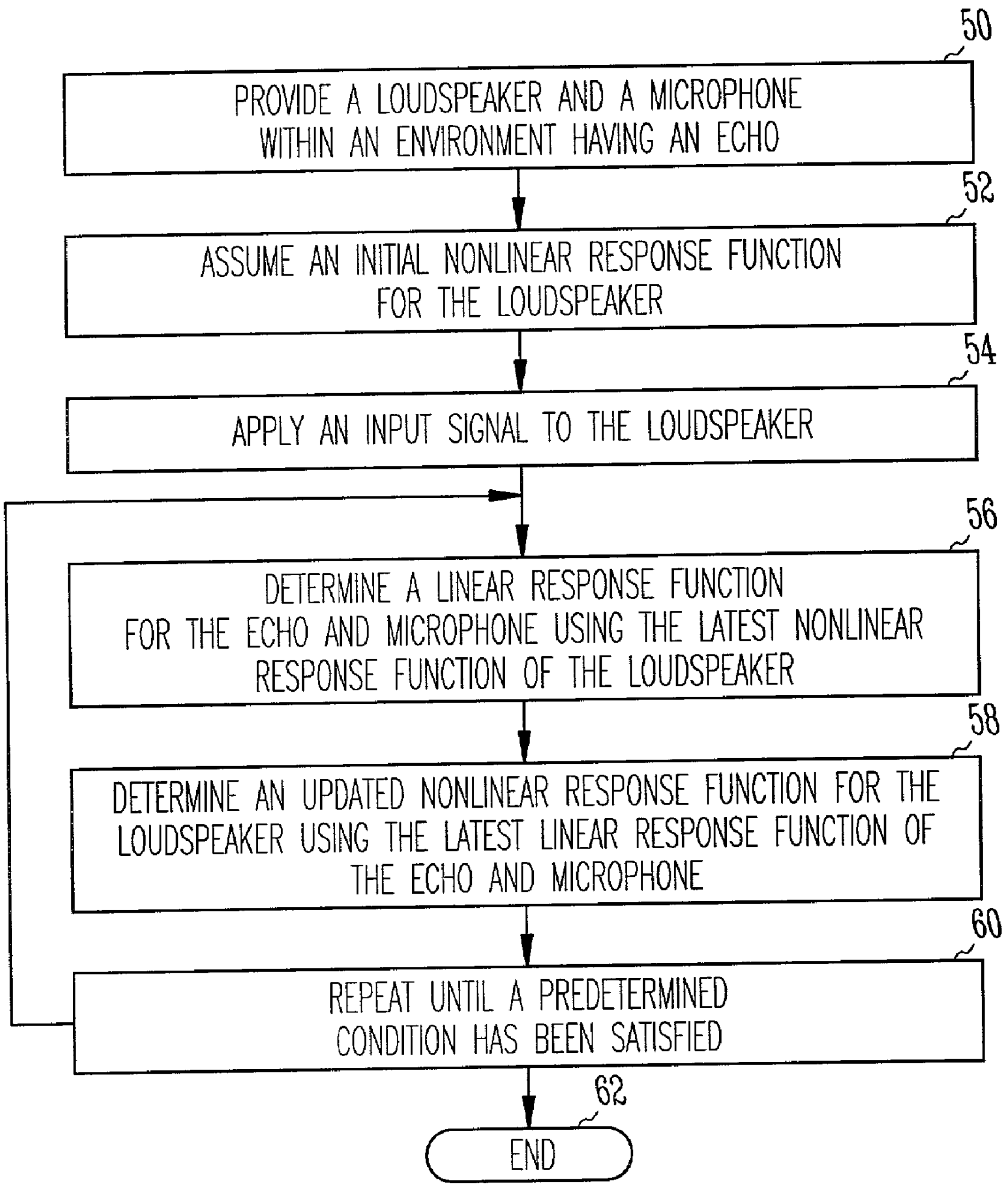
FIG. 3 is a flowchart illustrating a method for determining a nonlinear response function for a loudspeaker in accordance with an embodiment of the present invention.

FIG. 3 is a flowchart illustrating a method for determining a nonlinear response function for a loudspeaker in accordance with an embodiment of the present invention. The method can be used in connection with any application requiring knowledge of a loudspeaker response function and is not limited to mobile speaker phone applications. Significantly, the method does not require the use of an expensive test setup or anechoic chamber. In one approach, the method is performed in a manufacturing environment such as, for example, a manufacturing facility, to determine the response function of a loudspeaker either before or after the loudspeaker has been installed within a manufactured product. In another approach, the method is performed in the field (e.g., within an automobile) to calibrate or re- calibrate a loudspeaker that is part of an end user device.

A loudspeaker and microphone are first provided within an environment having an echo (block 50). The loudspeaker is the one for which a response function is desired. The microphone does not have to be the same or even a similar microphone to one that will be used with the loudspeaker in the field. Similarly, the echo response within the calibration environment does not have to be similar to the echo response that will be experienced in the field, nor does the echo response have to be known a priori. An initial nonlinear response function is next assumed for the loudspeaker (block 52). Preferably, the initial nonlinear response function that is used for the loudspeaker will be one that is believed to approximate the actual response function of the loudspeaker. For example, in one implementation, an average nonlinear response function for loudspeakers of the same type (e.g., same model) is used as the initial nonlinear response function. In one approach, a nonlinear Volterra filter response is used for the loudspeaker. A Volterra filter response of order 3 is expressed as follows:

$$y_n = \sum_{i=0}^{p1} b_i x_{n-i} + \sum_{i>j=0}^{p2} b_{ij} x_{n-i} x_{n-j} + \sum_{i>j>k=0}^{p3} b_{ijk} x_{n-i} x_{n-j} x_{n-k}$$

where $y_n$ is the output of the filter, x is the input of the filter, b are the filter coefficients, and p1, p2, and p3 are the lengths of the respective filter parts.

An input signal is next applied to the loudspeaker (block 54). In one approach, a noise generator is used to apply a noise signal to the loudspeaker that is within an audio frequency range. Other types of input signal are also possible. In response to the input signal, the loudspeaker will generate an audible output signal, part of which will be sensed by the microphone as an echo. As a result, the microphone will generate an echo signal at an output thereof. This echo signal may be digitized and stored for later use.

A linear response function is next determined for the combination of the echo and the microphone using the latest nonlinear loudspeaker response function (block 56). At this point, the latest nonlinear response function of the loudspeaker is the initial nonlinear response function that was assumed previously. In one embodiment, the linear response function is modeled as follows:

$$z_n = \sum_{i=0}^{p} a_i y_{n-i}$$

where $z_n$ is the output of the microphone, $y_n$ is the output of the loudspeaker, $a_n$ are the coefficients of the response function, and p is the length of the response function. In a preferred approach, a cost function minimization process is used to determine the coefficients ($a_i$) of the linear response function. First, the initial nonlinear response function is used to estimate the output signal of the loudspeaker ($y_n$) using the known input signal of the loudspeaker ($x_n$). The output signal ($z_n$) of the microphone is known (e.g., measured). To find the coefficients ($a_i$) of the linear response function of the echo/microphone, the following cost function is minimized:

$$F_1=\Sigma_n(Z_n-\Sigma_i a_1 Y_{n-i})^2$$

This represents a standard linear minimization problem that finds the minimum of a concave function and can be solved using a well known approach.

After the linear response function of the echo/microphone has been determined, an updated nonlinear response function is determined for the loudspeaker using the latest linear response function (block 58). As before, a cost function minimization process is preferably used to determine the coefficients $b_n$ of the revised nonlinear response function of the loudspeaker. It can be shown that, if the coefficients $a_n$ of the echo/microphone are known, then the function to be minimized to determine the coefficients $b_n$ of the nonlinear response is also a concave function. The Volterra filter response described previously can be represented as follows:

$$Y_{1=BX1}=\Sigma_{mBmXlm}$$

where B represents all coefficients of the nonlinear response function and X represents all combinations of x's that participate in the calculation of Y. We now define:

$$T_{nm}=\Sigma_j a_j X_{n-j,m}$$

This definition allows the cost function to be minimized to be expressed as:

$$F_2=\Sigma_n(Z_n-\Sigma_m b_m T_{nm})^2$$

Again, this represents a standard minimization problem that can be solved using a well known approach.

The linear response function of the echo/microphone and the nonlinear response function of the loudspeaker are now repeatedly and alternately redetermined in an iterative process until a predetermined condition has been satisfied (block 60). With each iteration, the linear response function of the echo/microphone and the nonlinear response function of the loudspeaker should each converge toward the actual responses. In one embodiment, the update process is repeated until no further improvement is being achieved in cost function $F_2$ on successive iterations. In another embodiment, the update process is repeated until a predetermined value of cost function $F_2$ has been achieved. In yet another embodiment, a predetermined number of iteration are performed. As will be appreciated, many alternative conditions or combinations of conditions for ending the iterative process can be used. After the iterative process has ended (block 62), the resulting nonlinear response function of the loudspeaker is recorded.

Figure 4:
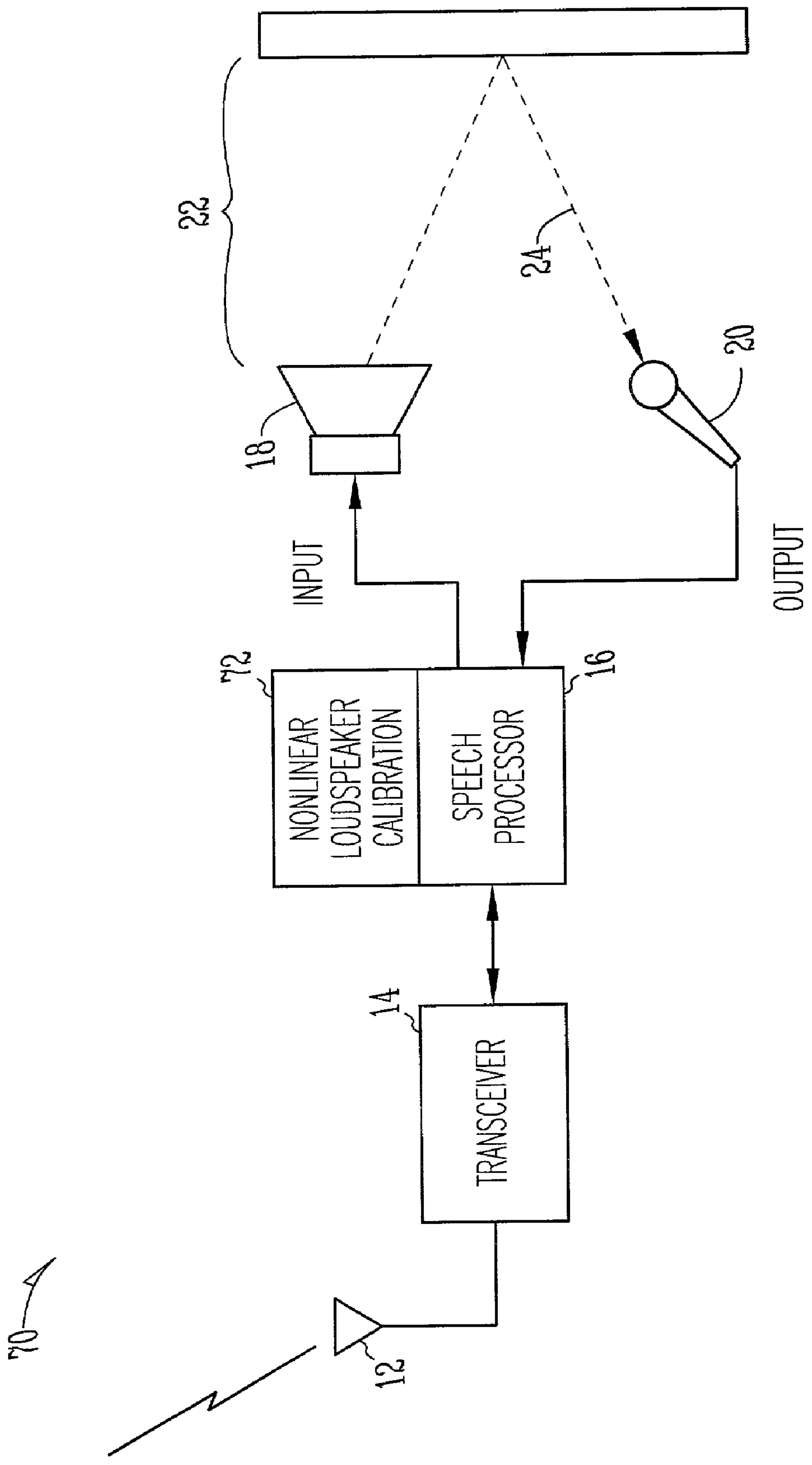
FIG. 4 is a block diagram illustrating a mobile speaker phone system having loudspeaker calibration functionality in accordance with an embodiment of the present invention.

FIG. 4 is a block diagram illustrating a mobile speaker phone system 70 having loudspeaker calibration functionality in accordance with an embodiment of the present invention. As illustrated, the mobile speaker phone system 70 of FIG. 4 is similar to the system 10 of FIG. 1. However, a loudspeaker calibration unit 72 has been added to the system to allow the nonlinear response function of the loudspeaker 18 to be updated in the field. If the original loudspeaker 18 is repaired or replaced, a new nonlinear response function will often be necessary to perform accurate echo cancellation. Similarly, as the loudspeaker 18 ages, the response of the loudspeaker 18 can drift which may also require the generation of a new nonlinear response function. The loudspeaker calibration unit 72 can be programmed to activate automatically during periods when the system 70 is off-line. Alternatively, or in addition, end user activation capabilities can be provided to allow an end user to initiate a recalibration.

In a preferred approach, the loudspeaker calibration unit 72 will be programmed to perform an iterative loudspeaker calibration technique, such as the method of FIG. 3. The loudspeaker calibration unit 72 can be implemented, for example, as a software routine that is executed within a digital processing device within the system 70. Hardware and hybrid hardware/software implementations are also possible. In one embodiment, the loudspeaker calibration unit 72 includes a signal source (e.g., a noise source) for providing an input signal to the loudspeaker 18 during calibration activities. After a new nonlinear response function has been generated for the loudspeaker 18, the loudspeaker calibration unit 72 will typically store the function (e.g., the coefficients of the Volterra filter) for later use during echo cancellation operations. Similar loudspeaker calibration functionality can be implemented within other types of systems that may require an accurate model of a loudspeaker response function, such as, for example, stationary (desktop) speaker phones and intercom systems.

Although the present invention has been described in conjunction with certain embodiments, it is to be understood that modifications and variations may be resorted to without departing from the spirit and scope of the invention as those skilled in the art readily understand. Such modifications and variations are considered to be within the purview and scope of the invention and the appended claims.

What is claimed is:

1. A method for determining a nonlinear response function for a loudspeaker, comprising:

providing a loudspeaker and a microphone within an environment having an echo;

assuming an initial nonlinear response function for said loudspeaker;

determining a linear response function for a combination of said echo and said microphone using a latest nonlinear response function of said loudspeaker; and determining a revised nonlinear response function for said loudspeaker using a latest linear response function of said combination.

2. The method of claim 1, further comprising:

repeating determining a linear response function and determining a revised nonlinear response function until a predetermined condition is satisfied.

3. The method of claim 2, wherein:

determining a revised nonlinear response function for said loudspeaker includes minimizing a cost function, wherein said predetermined condition includes achieving a predetermined value for said cost function.

4. The method of claim 2, wherein:

determining a revised nonlinear response function for said loudspeaker includes minimizing a cost function, wherein said predetermined condition includes achieving little further reduction in said cost function with each additional repetition.

5. The method of claim 1, wherein:

determining a linear response function includes minimizing a first cost function and determining a revised nonlinear response function includes minimizing a second cost function.

6. The method of claim 1, wherein:

said initial nonlinear response function of said loudspeaker is a Volterra filter response.

7. The method of claim 1, wherein:

said method is performed within a manufacturing facility.

8. The method of claim 1, wherein:

said loudspeaker is for use within a communication apparatus in a vehicle, said method being performed within said vehicle.

9. A method for determining a nonlinear response function for a loudspeaker, comprising:

providing a loudspeaker and a microphone within a vehicle having an echo;

assuming an initial nonlinear response function for said loudspeaker;

applying an input signal to said loudspeaker;

determining a linear response function for a combination of said echo and said microphone using a latest nonlinear response function for said loudspeaker; and determining a revised nonlinear response function for said loudspeaker a latest linear response function of said combination.

10. The method of claim 9, further comprising:

repeating determining a linear response function and determining a revised nonlinear response function until a predetermined condition is satisfied.

11. The method of claim 9, wherein:

determining a linear response function for a combination of said echo and said microphone includes minimizing a first cost function.

12. The method of claim 11, wherein:

said first cost function is:

$$F_1=\Sigma_n(Z_n-\Sigma_i a_i Y_{n-i})^2$$

where $Z_n$ is the output signal of the microphone, $a_n$ are the coefficients of the linear response function of the combination, and $Y_n$ is the estimated output signal of the loudspeaker.

13. The method of claim 9, wherein:

determining a revised nonlinear response function for said loudspeaker includes minimizing a second cost function.

14. The method of claim 13, wherein:

said second cost function is:

$$F_2=\Sigma_n(Z_n-\Sigma_m b_m T_{nm})^2$$

where $Z_n$ is the output signal of the microphone, $b_m$ are the coefficients of the nonlinear response function of the loudspeaker, and $$T_{nm}=\Sigma_j a_j X_{n-j,m}$$

where $a_j$ are the coefficients of the linear response function of the combination, and X is the input signal of the loudspeaker.

15. The method of claim 9, wherein:

said initial nonlinear response function of said loudspeaker is a Volterra filter response.

16. A communication apparatus, comprising:

a loudspeaker to generate an audible signal within an area using information received from a remote entity;

a microphone to generate an output signal based on sounds within said area, said output signal including information to be transmitted to said remote entity;

an echo suppression unit to reduce echos within said output signal of said microphone, said echo suppression unit using a nonlinear response function of said loudspeaker to reduce said echos; and a calibration unit to determine said nonlinear response function of said loudspeaker for use by said echo suppression unit wherein said calibration unit includes module for iteratively and alternately updating a linear response function of a combination of an echo and said microphone using a latest nonlinear response function of said loudspeaker and updating said nonlinear response function of said loudspeaker using a latest linear response function of said combination until a predetermined condition has been satisfied.

17. The communication apparatus of claim 16, wherein:

said calibration unit determines said nonlinear response function of said loudspeaker in the field.

18. The communication apparatus of claim 16, wherein:

said calibration unit includes a signal source for applying an input signal to said loudspeaker.

19. The communication apparatus of claim 18, wherein:

said signal source includes a noise generator.

20. The communication apparatus of claim 16, wherein:

said calibration unit includes a linear response module to determine said linear response function for said combination based on an assumed nonlinear response function of said loudspeaker.

21. The communication apparatus of claim 20, wherein:

said linear response module includes a minimization module for minimizing a first cost function.

22. The communication apparatus of claim 20, wherein:

said calibration unit includes a nonlinear response module to determine an updated nonlinear response function for said loudspeaker using said linear response function of said combination.

23. The communication apparatus of claim 22, wherein:

said nonlinear response module includes a minimization module for minimizing a second cost function.

24. The communication apparatus of claim 16, wherein:

said communication apparatus is a mobile speaker phone for use within a vehicle.

* * * * *

UNITED STATES PATENT AND TRADEMARK OFFICE

CERTIFICATE OF CORRECTION

PATENT NO. : 7,209,566 B2
APPLICATION NO. : 09/962503
DATED : April 24, 2007
INVENTOR(S) : Griniasty It is certified that error appears in the above-identified patent and that said Letters Patent is hereby corrected as shown below:

In column 8, line 19, in Claim 16, after “includes” insert -- a --.

On the Title page, Item [56] References Cited, delete the second occurrence of “Kaizer, A.J.M. Modeling of the Nonlinear Response of an Electrodynamic loudspeaker by a Volterra Series Expansion. Journal of the Audio Engineering Society, 35. Audio Engineering Society, New York (Jun. 1, 1987) pp. 421-433.”

Signed and Sealed this

Seventeenth Day of July, 2007

JON W. DUDAS
*Director of the United States Patent and Trademark Office*